United States Patent [19]

Gerhartl et al.

[11] Patent Number: 5,480,699

[45] Date of Patent: Jan. 2, 1996

[54] PAD FOR APPLYING LIQUID OR SEMI-SOLID MATERIAL

[75] Inventors: Gerd Gerhartl, Bichwil; Ernst Werner, Flawil, both of Switzerland

[73] Assignee: Flawa Schweizer Verbandstoff-und Wattefabrieken AG. Flawil, Flawil, Switzerland

[21] Appl. No.: 288,884

[22] Filed: Aug. 10, 1994

Related U.S. Application Data

[63] Continuation of Ser. No. 110,213, Aug. 23, 1993, abandoned, which is a continuation of Ser. No. 915,385, Jul. 20, 1992, abandoned, which is a continuation of Ser. No. 614,577, May 1, 1990, abandoned, which is a continuation of Ser. No. 96,307, Sep. 8, 1987, abandoned.

[30] Foreign Application Priority Data

Sep. 8, 1986 [CH] Switzerland .............................. 3592/86

[51] Int. Cl.⁶ .............................. B32B 5/14; B32B 27/00; B32B 27/34
[52] U.S. Cl. ..................... 428/171; 428/180; 428/192; 428/198; 428/284; 428/286; 428/287; 428/296; 428/298; 424/446; 424/447; 424/443
[58] Field of Search .................... 428/171, 180, 428/192, 198, 284, 286, 287, 224, 296, 298; 424/446, 447, 443

[56] References Cited

U.S. PATENT DOCUMENTS

| | | | |
|---|---|---|---|
| 1,961,914 | 6/1934 | Richter et al. | 428/194 |
| 3,088,463 | 5/1963 | Harmon | 428/224 |
| 3,310,454 | 11/1962 | Florio et al. | 428/171 |
| 3,616,157 | 10/1971 | Smith | 428/171 |
| 3,726,750 | 5/1971 | Stillings | 428/198 |
| 3,732,867 | 5/1973 | Money | 128/290 R |
| 3,804,092 | 4/1974 | Tunc | 428/224 |
| 3,949,130 | 4/1976 | Sabee et al. | 428/192 |
| 3,953,638 | 4/1976 | Kemp | 428/298 |
| 4,018,646 | 4/1977 | Ruffo et al. | 428/245 |
| 4,259,958 | 4/1981 | Goodbar | 428/289 |
| 4,326,000 | 4/1982 | Roberts, Jr. | 428/153 |
| 4,390,585 | 6/1983 | Holden | 428/246 |
| 4,443,512 | 4/1984 | Delvaux | 428/171 |
| 4,481,243 | 11/1984 | Allen | 428/194 |
| 4,496,358 | 1/1985 | Karami et al. | 604/379 |
| 4,526,825 | 7/1985 | Whitehead | 428/194 |
| 4,550,035 | 10/1985 | Smith | 427/398.1 |
| 4,569,343 | 2/1986 | Kimura et al. | 424/447 |
| 4,576,853 | 3/1986 | Vaughn et al. | 428/181 |
| 4,603,070 | 7/1986 | Steel et al. | 428/194 |
| 4,844,965 | 7/1989 | Foxman | 428/286 |
| 4,888,229 | 12/1989 | Paley et al. | 428/192 |

FOREIGN PATENT DOCUMENTS

| 530872 | 9/1956 | Canada | 428/171 |
|---|---|---|---|

*Primary Examiner*—Geroge F. Lesmes
*Assistant Examiner*—Terrel Morris
*Attorney, Agent, or Firm*—Browdy and Neimark

[57] ABSTRACT

The pad, of round or polygonal shape, has two compressed outer surfaces, and an entirely or nearly uncompressed body. The more highly compressed the surfaces, the less permeable the pad becomes to liquids and substances having the consistency of a salve. The pads are suitable for applying and/or absorbing liquid or semi-liquid materials in cosmetics, medicine end numerous fields of technology.

17 Claims, No Drawings

PAD FOR APPLYING LIQUID OR SEMI-SOLID MATERIAL

This application is a continuation of application Ser. No. 08/110,213, filed on Aug. 23, 1993, which is a continuation of 07/915,385, filed on Jul. 20, 1992, which is a continuation of 07/614,577, filed on May 1, 1990, which is a continuation of 07/096,307, filed on Sep. 8, 1987, now abandoned.

BACKGROUND OF THE INVENTION

Pads of round or polygonal shape made of cotton mat or similar material have become common articles in hygiene, cosmetics, and medicine. The products available previously on the market, while they were satisfactory in terms of absorbency and softness, had the undesirable tendency to lose fibers, so that fibers of the batting remained on the skin.

It has already been proposed that this disagreeable feature be eliminated by mixing thermoplastic fibers with the cotton or similar fibers and fusing them at various points to the outer surface of the cotton pad (European Patent 0 124 834). European Patent 0 135 404 also proposes that the fibers in the cotton web be firmly held in the interior of the web as well, by what is known as "hydraulic wrapping", in such a way that they can no longer readily come loose. Finally, it is known from German Utility Model 85 33 322 that a swab, made of cotton and/or viscose fibers, may be made by adding synthetic melting fibers to it, which are distributed over the entire volume of the tip and are joined to the fibers adjoining them by means of an at least superficial pressure-free fusion process.

SUMMARY OF THE INVENTION

The present invention now makes it possible in a simple and economical manner to produce "tailor-made" pads that suit various purposes and can be adapted to the various wishes of the consumer.

The pads according to the invention, which are intended in particular for applying and/or absorbing liquid or semi-solid substances such as cosmetic, pharmaceutical and biological fluids, salves, exudates, and so forth, as well as technical substances of every kind, have at least two plies, at least one layer being absorbent and both outer layers being compressed. Preferably they have a compressed surface layer on both sides with an approximately uncompressed or only slightly compressed and fully absorbent intermediate layer. The compression may be to an equal extent on both outer surfaces, or to different extents; in either case, however, it prevents lint formation, that is, the undesirable escape of individual fibers, and what is known as "powdering." For example, a liquid or cream can be applied without a great amount thereof penetrating the pad and thus being wasted. A lesser Compression on the back of the same pad, on the other hand, makes it possible to remove any excess substance applied, such as cleansing cream, simply by turning the pad over; the less-compressed and therefore more-absorbent outer surface does not present any problems at all in terms of absorption. Optionally, at least one layer contains a cosmetic or medically active ingredient.

DETAILED DESCRIPTION OF PREFERRED EMBODIMENTS

The compression of the outer surfaces is generally effected by calandaring, and more closely- or widely-spaced embossed patterns can also be selected as needed. Depending on the material, the calandaring is generally peformed preferably at 100° to 200° C. at a pressure of up to 0.5 kg/cm$^2$, with a roller speed of 5–25 m/min. If up to 10% of the surface area is embossed, the result is an absorbent material that is suitable for absorbing fluids. With an increasing proportion of embossed surface area, the surface becomes less and less absorbent; the recessed portions of the embossed pattern can additionally serve as a kind of reservoir, while the raised areas can serve as the absorbent cushion.

The compression can also be accomplished with the aid of chemical substances, such as physiologically unobjectionable air- and moisture-permeable synthetic resins that do not irritate the skin, with which the outer surface is treated to a variable extent as needed. Such resins are known to one skilled in the art for producing various articles of batting of wadding suitable fiber materials include cotton, viscose, synthetic fibers, or mixtures of these.

For producing the cotton pads according to the present invention, the procedure is, for example, as follows:

Preparation of the fibers to make the card web is done in the usual manner, for example on carding, card brushing or similar suitable machines. Next, the card web is combined into at least three continuous card web faces having the desired total weight, and then the embossing of the first and second card web face with the patterns that are desired and are needed for the particular intended use is performed in a known manner. The three (or more) card web faces are then put together to form a structure of alternating embossed and uncompressed layers- The web-like structure thus obtained is now stamped or cut into the desired shape and packed in a suitable manner. Depending on the intended use, a further treatment, such as sterilization, impregnation with active ingredients, and so forth, can also be performed before or after the web is cut to size. This process makes it possible to use conventional equipment, and products having a smooth, fiber-free, non-powdering yet still soft outer surface and an absorbent closed-edge seam are produced.

However, production can also be done with known machines by aerodynamic or hydrodynamic methods.

If desired, the compressed outer surface layers can have further slightly compressed layers placed in between them, to increase the absorbency of the products.

A round pad for cosmetic purposes, having a thickness of approximately 3.7 mm, for instance, comprises an uncompressed middle part approximately 1.5 mm in thickness and one compressed upper and lower surface layer each, each of which is approximately 0.8 mm thick. These outer surfaces are both provided with a waffle pattern, one with a very close pattern and the other with a widely spaced pattern of this kind. The product feels very soft and fluffy, but does not become linty or dusty and has excellent absorbency on the coarsely-patterned, less-compressed side.

Production is done in the following manner, by way of example:

100% cotton combings, pure and bleached white, are prepared on a carding machine into a carb web. This card web is combineed into three continuous card web faces having a total weight of approximately 350 g/m$^2$. Two of these card web faces are separately compressed in an embossing calender and provided with a waffle pattern, which is done at a roller temperature of 150° C., a passage speed of 12 m/min, and a pressure of 1100 kg/20 cm linearly. The three card web faces are then combined into a sandwich-like structure in such a way that the two compressed, embossed faces form the outer surfaces and the third, practically uncompressed face, comes to rest in between these two surfaces. This web of material now travels beneath a stamp, and the desired circles are stamped out, and then stacked into a roll and packed in plastic bags.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A pad consisting essentially of:
    a first outer layer made of fibrous absorbent material having inner and outer surfaces wherein the outer surface of said first outer layer is embossed;
    a substantially uncompressed intermediate layer made of one ply of carded web fibrous absorbent material;
    a second outer layer made of fibrous absorbent material having inner and outer surfaces wherein the outer surface of said second outer layer is embossed;
    wherein the inner surface of said first outer layer and the inner surface of said second outer layer contact said intermediate layer;
    said intermediate layer being laterally coextensive with said first outer layer and said second outer layer;
    wherein the absorbent material is selected from the group consisting of cotton, viscose, synthetic fiber and mixtures thereof; and
    said pad being formed by assembling the first outer layer, the intermediate layer and the second outer layer and the resulting assembly is stamped, wherein said stamping unites said layers.

2. The pad according to claim 1 wherein at least one layer contains a cosmetically or medically active ingredient.

3. The pad according to claim 1 wherein the first outer layer and said second outer layer are embossed to the same extent.

4. The pad according to claim 1 wherein said first outer layer and said second outer layer are embossed to different extents.

5. The pad according to claim 1 wherein said first outer layer and said second outer layer are embossed with a pattern.

6. The pad according to claim 1 wherein said pattern is a waffle pattern.

7. The pad according to claim 1 wherein each of said layers is made of the same material.

8. The pad according to claim 1 wherein said first outer layer has a thickness of 0.8 mm and said second outer layer has a thickness of 1.5 mm.

9. A pad consisting essentially of:
    a first outer layer made of fibrous absorbent material having inner and outer surfaces;
    a second outer layer made of fibrous absorbent material having inner and outer surfaces;
    said first outer surface of said first outer layer being embossed;
    said first outer surface of said second outer layer being embossed;
    a substantially uncompressed intermediate layer comprising one ply of carded web fibrous absorbent material, said intermediate layer being laterally coextensive with the first outer layer and the second outer layer;
    wherein the inner surface of said first outer layer and the inner surface of said second outer layer contact said intermediate layer;
    the fibrous absorbent material is selected from the group consisting of cotton, viscose, synthetic fibers, and mixtures thereof;
    and a seam is located around the periphery of said pad wherein the edges of the pad are held closed.

10. The pad according to claim 9 wherein at least one layer contains a cosmetically or medically active ingredient.

11. The pad according to claim 9 wherein said first outer layer and said second outer layer are embossed to the same extent.

12. The pad according to claim 9 wherein said first outer layer and said second outer layer are embossed to different extents.

13. The pad according to claim 9 wherein said first outer layer and said second outer layer are embossed with a pattern.

14. The pad according to claim 13 wherein said pattern is a waffle pattern.

15. The pad according to claim 9 wherein each of said layers is made of the same material.

16. The pad according to claim 9 wherein said first outer layer has a thickness of about 0.8 mm and said second outer layer has a thickness of about 1.5 mm.

17. A pad consisting essentially of:
    a first outer layer of fibrous absorbent material having inner and outer surfaces;
    a second outer layer of fibrous absorbent material having inner and outer surfaces;
    said first outer surface of said first outer layer being embossed;
    said first outer surface of said second outer layer being embossed;
    a substantially uncompressed intermediate layer comprising one ply of carded web fibrous absorbent material, said intermediate layer being laterally coextensive with the first outer layer and the second outer layer;
    a first secondary layer having inner and outer surfaces disposed between said first outer layer and said intermediate layer;
    a second secondary layer having inner and outer surfaces and being disposed between said second outer layer and said intermediate layer;
    wherein the inner surface of said first secondary layer and the inner surface of said second secondary layer contact said intermediate layer;
    the fibrous absorbent material is selected from the group consisting of cotton, viscose, synthetic fibers, and mixtures thereof;
    and a seam is located around the periphery of said pad wherein the edges of the pad are held closed.

* * * * *